(12) United States Patent
Kuesel

(10) Patent No.: US 8,983,027 B2
(45) Date of Patent: Mar. 17, 2015

(54) SYSTEM FOR THE NON-DESTRUCTIVE INSPECTION OF A CONVEYOR BELT VIA HIGH-ENERGY RADIATION

(71) Applicant: Phoenix Conveyor Belt Systems GmbH, Bad Blankenburg (DE)

(72) Inventor: Bernd Kuesel, Hamburg (DE)

(73) Assignee: Phoenix Conveyor Belt Systems GmbH, Bad Blankenburg (DE)

( * ) Notice: Subject to any disclaimer, the term of this patent is extended or adjusted under 35 U.S.C. 154(b) by 200 days.

(21) Appl. No.: 13/656,439

(22) Filed: Oct. 19, 2012

(65) Prior Publication Data

US 2013/0077743 A1   Mar. 28, 2013

Related U.S. Application Data

(63) Continuation of application No. PCT/EP2011/051717, filed on Feb. 7, 2011.

(30) Foreign Application Priority Data

Apr. 19, 2010 (DE) .......................... 10 2010 016 502

(51) Int. Cl.
*G01V 5/00* (2006.01)
*B65G 43/02* (2006.01)

(52) U.S. Cl.
CPC .......... *B65G 43/02* (2013.01); *G01N 2223/643* (2013.01)
USPC ........................................... 378/57; 378/209

(58) Field of Classification Search
USPC .................................................. 378/57, 209
See application file for complete search history.

(56) References Cited

U.S. PATENT DOCUMENTS

| | | | |
|---|---|---|---|
| 6,973,161 B2 | 12/2005 | Ohtsuki | |
| 7,427,767 B2 | 9/2008 | Kemp | |
| 7,438,252 B2 | 10/2008 | Kuesel | |
| 8,149,989 B2 | 4/2012 | Schnell | |
| 2008/0298547 A1* | 12/2008 | Kabumoto | ...................... 378/57 |

FOREIGN PATENT DOCUMENTS

| | | |
|---|---|---|
| DE | 35 17 314 A1 | 1/1986 |
| JP | 4-158208 A | 6/1992 |
| JP | 2000-292371 A | 10/2000 |
| WO | WO 01/09596 A1 | 2/2001 |
| WO | WO 2008/034483 A1 | 3/2008 |
| WO | WO 2009/101772 A1 | 8/2009 |

OTHER PUBLICATIONS

International Search Report dated Apr. 7, 2011 of international application PCT/EP 2011/051717 on which this application is based.

* cited by examiner

*Primary Examiner* — Hoon Song
(74) *Attorney, Agent, or Firm* — Walter Ottesen P.A.

(57) ABSTRACT

A system for the non-destructive inspection of a conveyor belt which includes a cover on the carrying side, a cover on the backing side, each cover being made of elastomeric material, and embedded tension members. While the conveyor belt is moving, a radiation source emits rays to the belt surface which are of such high energy that the rays pass through the belt within a region free of material disposed on the belt. A sensor detects the rays passing through the belt. A processor is operatively connected to the sensor and evaluates the result of the radiographic check. The radiation source and the sensor are accommodated in a housing, wherein, between the radiation source and the sensor, there are two housing openings through which the moving belt runs without contact.

20 Claims, 3 Drawing Sheets

SYSTEM FOR THE NON-DESTRUCTIVE INSPECTION OF A CONVEYOR BELT VIA HIGH-ENERGY RADIATION

CROSS REFERENCE TO RELATED APPLICATIONS

This application is a continuation application of international patent application PCT/EP2011/051717, filed Feb. 7, 2011, designating the United States and claiming priority from German application 10 2010 016 502.6, filed Apr. 19, 2010, and the entire content of both applications is incorporated herein by reference.

FIELD OF THE INVENTION

The invention relates to a system for the nondestructive inspection of a conveyor belt. The conveyor belt includes a cover on the carrying side and a cover on the running or back side and each cover is made of an elastomeric material. The conveyor belt further comprises embedded tension members. While the conveyor belt is moving, a radiation source emits rays in the direction of the belt surface which are of such high energy that the rays radiate through the conveyor belt within a material-free region, where a sensor detects, without contact, the rays which have passed through, where furthermore a process computer evaluates the result of the radiographic check.

BACKGROUND OF THE INVENTION

A system of this type is described in particular in the following patent literature: DE 35 17 314 A1; U.S. Pat. No. 8,149,989 B2; JP 04158208 A (Patent Abstracts of Japan); JP 2000292371 A (Patent Abstracts of Japan).

Conveyor belts are subject to high stresses resulting from external damage, in particular by the material conveyed, foreign bodies, chutes and scrapers. Furthermore, it is possible for internal problems relating to the tension members to occur, such as cord breaks or corrosion. Continuous monitoring of the state of conveyor belts is imperative for trouble-free operation. Damage that threatens the operation must be reported without delay.

There are a large number of systems for examining conveyor belts that are in operation, for example by means of optoelectronic or magneto-inductive methods or by using laser or x-ray systems. In most cases, inspection is carried out only by means of visual monitoring by a person.

Each of the previously known methods has advantages and disadvantages. However, none has hitherto been useful for the detection of both internal and external conveyor belt damage.

SUMMARY OF THE INVENTION

The object of the invention is, then, to develop the system according to U.S. Pat. No. 8,149,989 in such a way that detection of both internal and external conveyor belt damage is possible. The intention is also hereby to detect the position and geometry of the tensile members that are vulcanized into the conveyor belt, in particular in the form of tensile member cords, and also for foreign bodies to be detected. Furthermore, the inspection should be capable of performance without interference from external influences and in an environmentally friendly manner.

This object is achieved in that the radiation source and the sensor are accommodated in a housing, wherein, between the radiation source and the sensor, there are two housing openings through which the moving conveyor belt runs without contact.

The radiation source emits in particular x-rays and is especially in the form of an x-ray tube. Within the housing, the radiation source is arranged in such a way that the belt surface can be detected by the rays in accordance with the following three variants I, II or III:

Variant I

The radiation source detects the whole width of the conveyor belt. This is preferably the case when the conveyor belt is not excessively wide, for example up to 1000 mm.

Variant II

The radiation source detects only the central region of the conveyor belt, which is particularly affected by impact damage. For example, if the conveyor belt is 2000 mm wide, then the central region, having a dimension of about 1000 mm, is detected.

Variant III

Large overland conveyor belts, for which the monitoring is of particular importance, are generally up to 2800 mm wide. Since, in particular, the x-ray tubes are comparatively expensive, the conveyor belt is divided up into longitudinal strips (segments) when a single x-ray tube is used. If, for example, the conveyor belt has a width of 2000 mm, the latter is divided up into four longitudinal strips each having a width of 500 mm. Following each revolution, the x-ray tube is displaced by 500 mm. A 2000 mm wide conveyor belt would then be recorded completely in four revolutions.

Opposite the radiation source, that is, on the other side of the moving conveyor belt, the rays are detected by sensors, also comprising light-sensitive chips. In order to obtain good resolution, for example 3 mm, even at a high speed of a conveyor belt, which is usually around 6 m/s, line sensors are preferably used. The sensor can, in addition, act as an individual sensor or as a sensor chain. The dimension of a sensor depends in particular on according to which of the three aforementioned variants I, II or III the radiation source detects the extent of the conveyor belt width. In the case of the variant III, a displaceable sensor can be employed.

The intensity of the rays received in conjunction with the subsequent evaluation of the gray scale values by means of specific image processing software permits conclusions to be drawn about the condition of the conveyor belt. For example, even indentations in the conveyor belt, which are filled with conveyed material, are detected by means of density differences.

The data relating to the points deviating from the satisfactory condition of the conveyor belt is ultimately evaluated in real time and, for example via individual threshold value data filters, automatically leads to error messages. In addition, the data is evaluated graphically.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
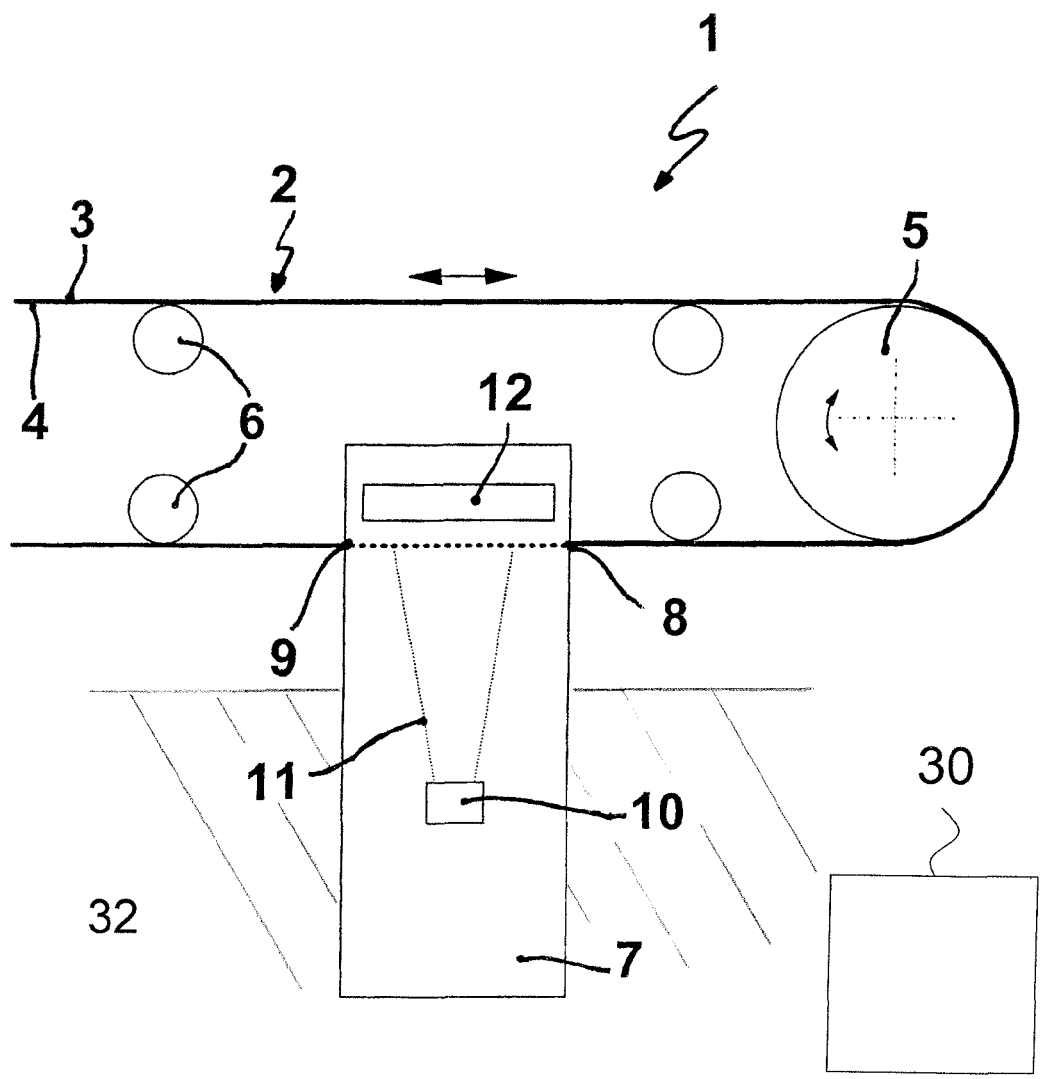
FIG. 1 shows the arrangement of a housing with integrated radiation source and sensor within a moving conveyor installation.

FIG. 1 shows a conveyor installation 1 having a conveyor belt 2. The conveyor belt comprises a cover 3 on the carrying side and a cover 4 on the backing side, each made of an elastomeric material, for example a vulcanized rubber mixture based on CR, and an embedded tension member. Tension members used in the conveyor belt are cords of steel or aramid running in the longitudinal direction, steel cords being of particular importance. Especially in conjunction with steel-cord conveyor belts, for the purpose of safeguarding against slits, in addition an embedded transverse armoring made of synthetic cords, for example polyamides, is used (WO2008/034483 A1). The tension member can also be a two-dimensional or flat textile structure, in particular a single-layer or multi-layer fabric, for example a polyester-polyamide fabric.

In the running direction (arrow direction), the conveyor belt 2 is led around a drum 5 (drive drum, reversal drum). The cover 4 is supported on the backing side thereof on carrier rollers 6.

Incorporated into the conveyor installation 1, within the lower run, is a housing 7 which has two housing openings (8, 9) through which the moving conveyor belt 2 is guided in the running direction at normal operating speed. The two housing openings are normally formed as appropriately large wide slots, through which the material-free conveyor belt can be led without contact.

Accommodated within the housing 7 is a radiation source 10, in particular, in the form of an x-ray tube. With its high-energy rays 11, in particular again in the form of x-rays, the radiation source detects the cover 3 on the carrying side. With regard to the detection, reference is made to the aforementioned three variants I, II or III. A sensor 12, which is arranged in the close vicinity of the cover 4 on the backing side, detects the rays 11 which have passed through, without contact (that is, without wear). The sensor here is in particular formed as a line sensor. A process computer 30 finally evaluates the result of the radiographic check.

The installation of the housing 7, in particular as a commercial x-ray device, is preferably carried out underneath the conveyor installation 1 for continuous use, specifically sunk into the ground 32. This is advantageous:

because the radiation 11 possibly emitted through the housing 7 is minimized by the surrounding earth;
because the conveyor belt 2 is free of contaminants there; and,
because the conveyor belt 2 there can be led horizontally through the housing 7, which is expedient for satisfactory radiography.

The x-ray device preferably used can be connected online without difficulty, so that additional evaluations of the data found are possible from any desired locations in the world.

Figure 2:
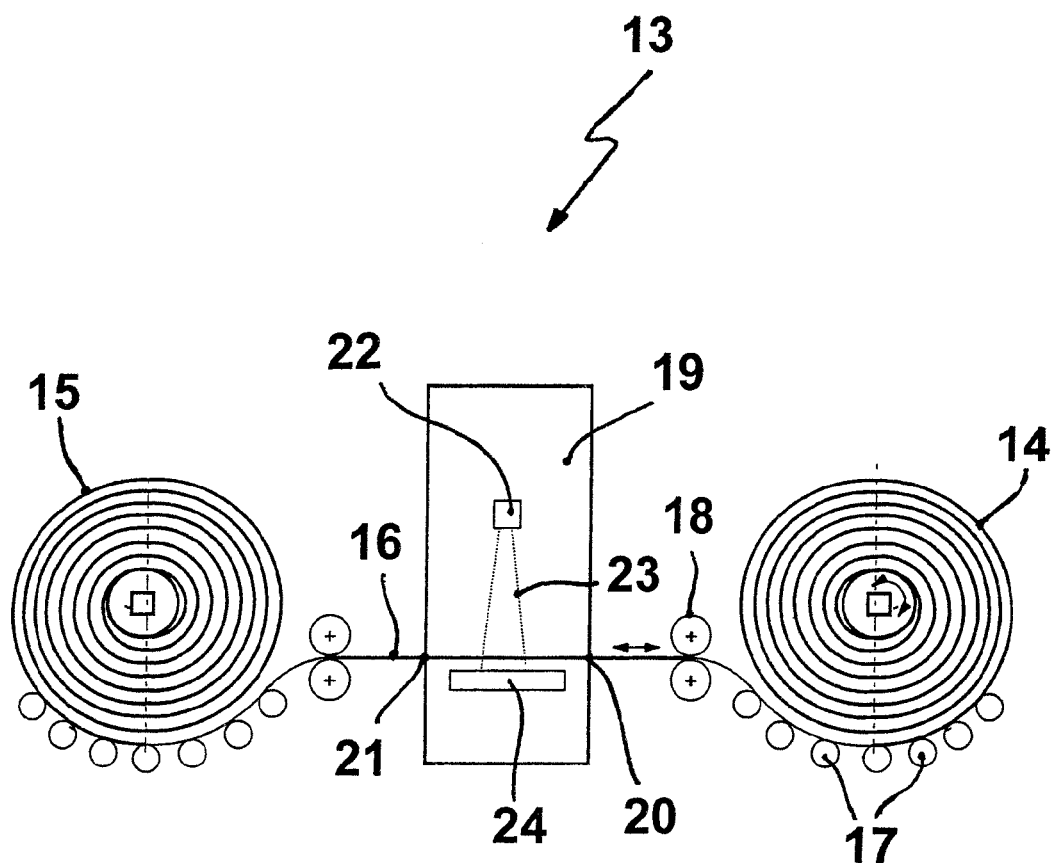
FIG. 2 shows the arrangement of a housing with integrated radiation source and sensor between two conveyor belt rolls as the conveyor belt is unwound and wound up; and, FIG. 3 shows a moving conveyor installation having two housings arranged at a distance from one another with each housing having an integrated radiation source and a sensor.

FIG. 2 now shows a conveyor belt winding system 13 having two conveyor belt rolls 14 and 15 for unrolling and rolling up a conveyor belt 16. In this case, each conveyor belt roll rests on a carrier roller system 17, for example in accordance with the teaching according to U.S. Pat. No. 7,438,252. The conveyor belt 16 is brought into the horizontal position by means of guide rollers 18.

In the conveyor belt winding system 13, a housing 19 is now incorporated between the two conveyor belt rolls 14 and 15, within the conveyor belt region running horizontally, and has two housing openings 20 and 21, through which the moving conveyor belt 16 is guided in the winding direction at normal winding speed. Here, too, the two housing openings are normally formed as appropriately large wide slots, through which the material-free conveyor belt can be led without contact.

Accommodated now within the housing 19 is a radiation source 22, in particular in the form of an x-ray tube. With its high-energy rays 23, in particular again in the form of x-rays, the radiation source detects the cover on the carrying side. With regard to the detection, reference is made in particular to the aforementioned variant I. A sensor 24, which is arranged in the close vicinity of the cover on the backing side, detects the rays 23 which have passed through, without contact (that is, without wear). The sensor in this case is in particular formed as a line sensor. A process computer finally evaluates the result of the radiographic check. The process computer can be operatively connected to the sensor and the radiation source.

The installation of the housing 19, in particular as a commercial x-ray device, can be integrated into a conveyor belt winding system 13, for example as early as during the manufacture of the latter, amongst other things within the context of a transportable conveyor belt winding system.

In FIGS. 1 and 2, a single housing with integrated radiation source and integrated sensor carries out the radiographic check, which is normally also sufficient. In the case of conveyor installations of large dimensions according to FIG. 1, it may be practical to use at least two housings, which are arranged at a comparatively great distance from one another. A monitoring check is also associated herewith.

Figure 3:
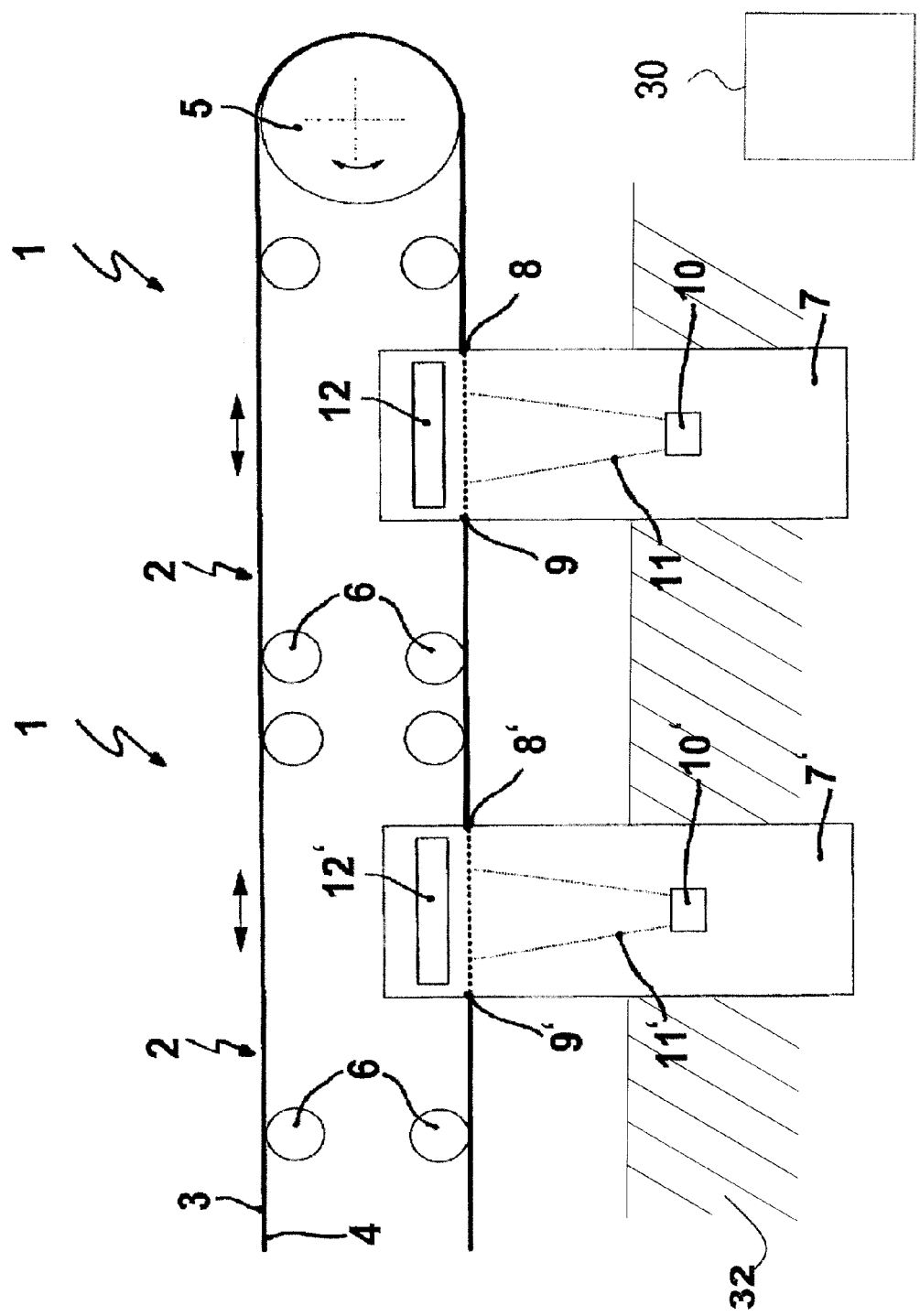

FIG. 3 shows such an installation of large dimensions in the form of a moving conveyor installation equipped with two housings (7, 7') arranged at a distance from one another. The additional housing 7' also includes an integrated radiation source 10' and integrated sensor 12'.

The housing 7 is a first housing, the radiation source 10 is a first radiation source integrated in the first housing 7, the sensor 12 is a first sensor integrated into the first housing 7, and the first housing 7 with the integrated radiation source 10 and the first sensor 12 is configured to without contact detect the rays 11 passing through the conveyor belt 2.

The system of FIG. 3 further includes: a second housing 7' which defines two second housing openings (8', 9'); a second radiation source 10' disposed in the second housing 7' and configured to emit rays 11' directed to the surface of the moving conveyor belt; the rays being so high in energy so as to pass through the conveyor belt in a region where no material is carried thereon; a second sensor 12' disposed in the second housing 7' and configured to without contact detect the rays 11' passing through the conveyor belt; the process computer being configured to evaluate the data from the first and the second sensors (12, 12'); and, the two second housing openings (8', 9') being disposed between the second radiation source 10' and the second sensor 12' and being configured to have the conveyor belt run through the openings without contact thereto.

It is understood that the foregoing description is that of the preferred embodiments of the invention and that various changes and modifications may be made thereto without departing from the spirit and scope of the invention as defined in the appended claims.

LIST OF DESIGNATIONS (Part of the Description)
1 Conveyor installation
2 Conveyor belt
3 Cover on the carrying side
4 Cover on the backing side 5 Drum
6 Carrier rollers
7 Housing
8 Housing opening
9 Housing opening
10 Radiation source
11 Rays
12 Sensor (Detector)
13 Conveyor belt winding system
14 Conveyor belt roll
15 Conveyor belt roll
16 Conveyor belt
17 Carrier roller system
18 Guide rollers
19 Housing
20 Housing opening
21 Housing opening
22 Radiation source
23 Rays
24 Sensor (Detector)
30 Process Computer
32 Ground

What is claimed is:

1. A system for nondestructive inspection of a moving conveyor belt of a conveyor installation, the moving conveyor belt defining a surface and including a carrying side cover made of elastomeric material, a running or back side cover made of elastomeric material and an embedded tension member, the conveyor belt having an upper run where materials are transported on said carrying side cover and a lower run where no materials are transported by the conveyor belt, the system comprising:
   a housing being mounted below said conveyor installation in the region of the lower run;
   said housing having two openings conjointly defining a clear uninterrupted space therebetween for passing said lower run through said housing;
   a radiation source disposed in said housing and configured to emit rays directed onto the surface of the moving conveyor belt;
   said rays being so high in energy so as to pass through the conveyor belt in a region of said conveyor belt where no material is disposed or transported thereon;
   a sensor disposed in said housing and configured to without contact detect said rays passing through the conveyor belt;
   a process computer configured to evaluate data from said sensor; and,
   wherein said two housing openings are disposed between said radiation source and said sensor and are configured to have the conveyor belt run through said openings without contact with said housing.

2. The system of claim 1, wherein said radiation source is configured to emit x-rays.

3. The system of claim 2, wherein said radiation source is an x-ray tube.

4. The system of claim 1, wherein:
   the conveyor belt has a predetermined width (a); and,
   said radiation source is arranged in said housing in such a manner that said radiation source covers the entire width (a) of the conveyor belt with said rays.

5. The system of claim 1, wherein said radiation source is arranged in said housing in such a manner that said radiation source covers said region of the conveyor belt with said rays.

6. The system of claim 1, wherein said radiation source is a displaceable radiation source configured to cover a longitudinal strip system of the conveyor belt with said rays.

7. The system of claim 1, wherein said radiation source covers the carrying side cover; and, said sensor covers said back side cover.

8. The system of claim 1, wherein said sensor is a line sensor.

9. The system of claim 1, wherein said sensor is a single sensor.

10. The system of claim 1, wherein said sensor is a sensor chain.

11. The system of claim 1, wherein said housing openings are wide slots.

12. The system of claim 1, wherein said housing is a part of the conveyor installation.

13. The system of claim 1, wherein said housing is arranged between two conveyor belt rolls.

14. The system of claim 1, wherein said radiation source and said sensor are integrated in a single housing configured to perform a check of the rays passing through the conveyor belt.

15. A system for nondestructive inspection of a moving conveyor belt of a conveyor installation, the moving conveyor belt defining a surface and including a carrying side cover made of elastomeric material, a running or back side cover made of elastomeric material and an embedded tension member, the conveyor belt having an upper run where materials are transported on said carrying side cover and a lower run where no materials are transported by the conveyor belt, the system comprising:
   a housing being mounted below said conveyor installation in the region of the lower run;
   said housing having two openings for passing said lower run through said housing;
   a radiation source disposed in said housing and configured to emit rays directed onto the surface of the moving conveyor belt;
   said rays being so high in energy so as to pass through the conveyor belt in a region of said conveyor belt where no material is disposed or transported thereon;
   a sensor disposed in said housing and configured to without contact detect said rays passing through the conveyor belt;
   a process computer configured to evaluate data from said sensor;
   wherein said two housing openings are disposed between said radiation source and said sensor and are configured to have the conveyor belt run through said openings without contact with said housing;
   wherein said housing is a first housing, said radiation source is a first radiation source integrated in said first housing, said sensor is a first sensor integrated into said first housing, and said first housing with said integrated radiation source and said first sensor is configured to without contact detect the rays passing through the conveyor belt; said system further comprising:
   a second housing which defines two second housing openings;
   a second radiation source disposed in said second housing and configured to emit rays directed to the surface of the moving conveyor belt;
   said rays being so high in energy so as to pass through the conveyor belt in a region where no material is carried thereon;
   a second sensor disposed in said second housing and configured to without contact detect said rays passing through the conveyor belt;
   said process computer being configured to evaluate the data from said first and said second sensors; and, said two second housing openings being disposed between said second radiation source and said second sensor and being configured to have said lower run pass through said two second housing openings without contact thereto.

16. A system for nondestructive inspection of a moving conveyor belt of a conveyor installation, the moving conveyor belt defining a surface and including a carrying side cover made of elastomeric material, a running or back side cover made of elastomeric material and an embedded tension member, the conveyor belt having an upper run where materials are transported on said carrying side cover and a lower run where no materials are transported by the conveyor belt, the system comprising:

a housing being mounted below said conveyor installation in the region of the lower run;
said housing having two openings for passing said lower run through said housing;
a radiation source disposed in said housing and configured to emit rays directed onto the surface of the moving conveyor belt;
said rays being so high in energy so as to pass through the conveyor belt in a region of said conveyor belt where no material is disposed or transported thereon;
a sensor disposed in said housing and configured to without contact detect said rays passing through the conveyor belt;
a process computer configured to evaluate data from said sensor;
wherein said two housing openings are disposed between said radiation source and said sensor and are configured to have the conveyor belt run through said openings without contact with said housing; and,
said housing is in the ground.

17. The system claim 1, wherein said housing is in the ground.

18. A conveyor installation comprising:
a drum;
a moving conveyor belt led around said drum to define an upper run whereon materials are transported and a lower run whereon no materials are transported;
said conveyor belt including a carrying side cover made of elastomeric material and a running or back side cover made of elastomeric material and an embedded tension member;
a system for nondestructively inspecting said moving conveyor belt;
a housing mounted in the region of said lower run;
said housing having two openings conjointly defining a clear uninterrupted space therebetween for passing said lower run through said housing;
a radiation source disposed in said housing and configured to emit rays directed onto the surface of said lower run of said moving conveyor belt;
said rays being so high in energy so as to pass through said lower run of said conveyor belt;
a sensor disposed in said housing and configured to without contact detect said rays passing through said conveyor belt;
a process computer configured to evaluate data from said sensor; and,
wherein said two housing openings are disposed between said radiation source and said sensor and are configured to have the conveyor belt run through said openings without contact with said openings.

19. The conveyor installation of claim 18, wherein said housing is a first housing, said radiation source is a first radiation source integrated in said first housing, said sensor is a first sensor integrated into said first housing, and said first housing with said integrated radiation source and said first sensor is configured to without contact detect the rays passing through the conveyor belt; said system further comprising:

a second housing which defines two second housing openings conjointly defining a clear uninterrupted space therebetween for passing said lower run therethrough;
a second radiation source disposed in said second housing and configured to emit rays directed to the surface of the moving conveyor belt;
said rays being so high in energy so as to pass through the conveyor belt in a region where no material is carried thereon;
a second sensor disposed in said second housing and configured to without contact detect said rays passing through the conveyor belt;
said process computer being configured to evaluate the data from said first and said second sensors; and, said two second housing openings being disposed between said second radiation source and said second sensor and being configured to have said lower run pass through said two second housing openings without contact thereto.

20. The conveyor installation of claim 18, wherein said housing is in the ground.

* * * * *